United States Patent [19]

Vinas

[11] Patent Number: 4,618,625
[45] Date of Patent: Oct. 21, 1986

[54] ZINC CARBOCYSTEINATE

[75] Inventor: Antonio B. Vinas, Barcelona, Spain

[73] Assignee: Laboratorios Vinas, S.A., Barcelona, Spain

[21] Appl. No.: 636,201

[22] Filed: Jul. 31, 1984

[30] Foreign Application Priority Data

Aug. 8, 1983 [ES] Spain .................................. 524820

[51] Int. Cl.$^4$ .............................................. C07F 3/06
[52] U.S. Cl. .................................... 514/494; 556/134
[58] Field of Search ................... 260/429.9; 514/494; 556/134

[56] References Cited

U.S. PATENT DOCUMENTS

| | | | |
|---|---|---|---|
| 2,745,859 | 5/1956 | Norton et al. | 260/429.9 |
| 2,840,587 | 6/1958 | Norton | 260/429.9 |
| 2,872,469 | 2/1959 | Stevens | 260/429.9 |
| 3,624,143 | 11/1971 | Shen | 260/429.9 X |
| 3,647,834 | 3/1972 | Martin | 260/429.9 |
| 3,803,138 | 4/1974 | Bore | 260/429.9 X |

OTHER PUBLICATIONS

S-Carboxymethylcysteine, S. Yanaura, y col., Oyo Yakuri (1976) 12(5), 777-788.
Tratamiento de las enfermedades bronco-pulmonares no especifica en enfermos no hospitalizados con un nuevo preparado de cisteina, R. Glosauer, y col., Therapiewoche, 26, 6533-6536 (1976).
La carbocisteina nel trattamento della bronchite cronica e nella profilassi delle sue riacutizzazioni, Cellini F., y col., Lotta Contro la tubercolosi e le malattie polmonari sociali, No. 1, 1980, 1-10.

Primary Examiner—Helen M. S. Sneed
Attorney, Agent, or Firm—Flynn, Thiel, Boutell & Tanis

[57] ABSTRACT

A zinc carbocysteinate is disclosed which has the formula:

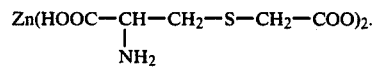

The zinc carbocysteinate of the present invention is useful for the treatment of skin conditions and respiratory infections and is made by reacting a zinc oxide, hydroxide or salt with carbocysteine.

3 Claims, No Drawings

ZINC CARBOCYSTEINATE

The present invention relates to the preparation of a salt of 3-[(carboxymethyl)thio]alanine, also known as carbocysteine and carboxymethylcysteine, and more specifically to the preparation of a zinc salt of carbocysteine having the formula:

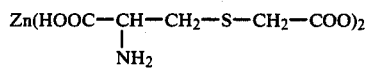

The foregoing zinc carbocysteinate, which is the subject of the present invention, possesses remarkable pharmaceutical properties, particularly as compared to other alkali metal and alkaline earth metal salts of carbocysteine and even in comparison with carbocysteine itself. The presence of zinc, a metal having a recognized pharmacological activity, is apparently the cause of the increased activity of the zinc carbocysteinate of the present invention.

Cysteine, and more particularly carboxymethylcysteine derivatives, have activity for the treatment of seborrhea, oily hair, sebaceous alopecia, exfoliative dermatitis, fingernail fragility and similar conditions. Such compounds have also been used as mucolytic expectorants in the treatment of respiratory conditions. In particular, carbocysteine is a known mucolytic, expectorant and nasal anti-infective agent.

Zinc is a well known oligoelement. A deficiency of zinc in the human body causes various problems, some of which have dermatologic manifestations. In particular, zinc has been used, by topical and oral application methods, for the treatment of alopecia, and also as a sebum secretion inhibitor. Clinical studies have suggested the use of zinc for the treatment of acne and similar skin conditions. Zinc has also been recognized to have mucosecretory and cytoprotectory properties, and is therefore potentially useful in treating respiratory diseases. As discovered in the present invention, the properties displayed by zinc carbocysteinate are different from and improved with respect to known carbocysteinate salts. The known pharmacological activities of carboxymethylcysteine are expanded by the discovery of the zinc salt thereof.

The present invention also pertains to a process for the preparation of zinc carbocysteinate. This process comprises reacting carbocysteine, or a watersoluble alkali or ammonium salt thereof, with a zinc salt, such as zinc acetate, zinc carbonate, zinc oxide or zinc hydroxide. The reaction is conducted using stoichiometric quantities of the foregoing two reactants in a 1:1 mole ratio. As a solvent for the reaction, a solvent for the foregoing two reactants is employed, which solvent is preferably a polar solvent or a mixture of polar solvents, most preferably water. The reaction temperature ranges from room temperature to the boiling temperature of the solvent. The zinc carbocysteinate precipitate is collected by filtration or centrifugation, and is then preferably washed and dried under vacuum.

The following nonlimiting examples illustrate the process used to make the compound of the present invention.

EXAMPLE 1

14.2 g of basic zinc carbonate are added gradually under stirring to a suspension of 35.8 g of carbocysteine (0.2 moles) in 360 ml water, and the resulting mixture is boiled at reflux for two hours. The precipitate formed by the reaction is separated by filtration, washed with water and then dried in a vacuum dessicator. 29 g of a white solid product were obtained.

Analysis: calculated for $C_{10}H_{16}O_8N_2S_2Zn$; % C 28.48; % H 3.83; % N 6.64; % S 15.20; % Zn 15.5. Found: % C 28.52; % H 4.26; % N 6.44; % S 15.35; % Zn 15.2. $LD_{50}$ mouse: 2660 mg/kg (oral) and 137 mg/kg (i.p.)

EXAMPLE 2

A solution of 44 g of zinc acetate in 150 ml of water is added to a suspension of 35.8 g carbocysteine and 300 ml water under stirring. The resulting mixture is boiled at reflux for two hours. The precipitate formed by the reaction is recovered as described above for Example 1. 35 g of a solid white product were obtained. This product had substantially the same analysis and $LD_{50}$ values as indicated in Example 1 above.

For therapeutic use, zinc carbocysteinate according to the present invention is normally administered as the essential active ingredient of a pharmaceutical composition comprising the zinc carbocysteinate and a pharmacologically acceptable carrier, diluent or vehicle. One or more other active ingredients may be incorporated in the pharmaceutical composition together with the zinc carbocysteinate. The carrier, diluent or vehicle can be a solid or liquid. Examples of useful solid vehicles include lactose, alba earth, saccharose, talc, gelatin, agar, pectin, acacia, magnesium stearate, stearic acid and similar known substances. Typical liquid vehicles include syrup, peanut oil, olive oil, water and the like. The pharmaceutical compositions according to the present invention can be formulated in any conventional form, such as tablets, hard gelatin capsules, powders, granules, capsules and others.

When a liquid vehicle is used, the pharmaceutical composition can be in the form of a syrup, emulsion, soft gelatin capsule, sterile liquid lotion, injectable ampules and aqueous or nonaqueous liquid suspensions, among others. Mixed vehicles can also be used so that the composition takes the form of a cream, pomade or a suppository. The foregoing pharmaceutical compositions are prepared by conventional formulation techniques, such as mixing, dissolution, or granulation and compression, as required for the desired preparation. The pharmaceutical composition according to the present invention is not limited as to the mode of administration, and can be administered orally, parenterally, topically or rectally. The dosage for an adult human being varies widely with the type of preparation and condition to be treated. In general, the daily dosage is an amount effective to treat any one of the following conditions in a human being: skin and hair conditions including seborrhea, alopecia, oily hair, acne, exfoliative dermatitis, respiratory infections or fingernail fragility. The dosage amount can also be an amount effective to achieve expectorant or mucolytic effects.

The embodiments of the invention in which an exclusive property or privilege is claimed are defined as follows:

1. A compound having the formula:

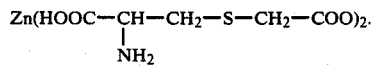

2. A pharmaceutical composition comprising an amount of a compound as claimed in claim 1 effective to treat hair or skin conditions including seborrhea, alopecia, oily hair, exfoliative dermatitis, acne or fingernail fragility, in combination with a pharmacologically acceptable carrier, diluent or vehicle.

3. A pharmaceutical composition comprising an amount of a compound as claimed in claim 1 effective to treat a respiratory infection, in combination with a pharmacologically acceptable carrier, diluent or vehicle.

* * * * *